US00PP11293P

United States Patent [19]

Zary

[11] Patent Number: Plant 11,293

[45] Date of Patent: Mar. 14, 2000

[54] GRANDIFLORA ROSE PLANT NAMED 'JACZOR'

[75] Inventor: Keith W. Zary, Thousand Oaks, Calif.

[73] Assignee: Bear Creek Gardens, Inc., Medford, Oreg.

[21] Appl. No.: 09/001,481

[22] Filed: Dec. 31, 1997

[51] Int. Cl.[7] ..... A01H 5/00

[52] U.S. Cl. ..... Plt./139

[58] Field of Search ..... Plt./139, 140

*Primary Examiner*—Howard J. Locker

*Attorney, Agent, or Firm*—Klarquist Sparkman Campbell Leigh & Whinston, LLP

[57] ABSTRACT

Grandiflora rose having large, red flowers presented in open clusters with long vase life; resistance to rust and powdery mildew; a vigorous, well-branched growth habit; and dark green foliage.

1 Drawing Sheet

The present invention relates to a new and distinct variety of rose plant of the grandiflora class which was originated by me by crossing the variety 'JACient', U.S. Plant Pat. No. 6725, with the variety 'Zorina', U.S. Plant Pat. No. 2321.

The primary objective of this breeding was to produce a new rose variety having the vigorous, somewhat rounded plant habit and disease resistant dark green foliage of the female parent combined with the heavy petal substance and long vase life of the male parent. The objective was substantiallyachieved, along with other desirable improvements, as evidenced by the following unique combination of characteristics that are outstanding in the new variety and that distinguish it from its parents, as well as from all other varieties of which I am aware:

1. Long vase life for a garden rose (over 14 days);
2. Vigorous, well-branched habit of growth;
3. Dark green, semi-glossy foliage;
4. Resistance to powdery mildrew and rust;
5. Flowers presented in large open clusters.

JACzor is a vigorous grandiflora that breaks freely from the bud union forming a plant as wide as it is tall. It flowers continuously during the growing season forming large open clusters so that each flower can open fully.

Asexual reproduction of this new variety by budding, as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACient (U.S. Plant Pat. No. 6,725).

*Pollen parent.*—Zorina (U.S. Plant Pat. No. 2,321).

Classification:

*Botanical.*—Rosa hybrida.

*Commerical.*—Grandiflora.

FLOWER

Observations made from specimens grown in a garden environment at Somis, Calif. from Jan., 1996 –Aug., 1997.

Blooming habit: Continuous.

Bud:

*Size.*—One and three-fourth inches long when the petals start to unfurl.

*Form.*—The bud form is long, pointed ovoid.

*Color.*—When sepals first divide, bud color is Red Group 46C, often with light pink blotch on outer petals. When half blown, the upper sides of the petals are Red Group 46C; and the lower sides of the petals are Red Group 46C.

*Sepals.*—Color: Green group 138B. Surface texture: Covered with fine hairs. There are three normally to heavily appendaged sepals. There are two unappendaged sepals with hairy edges.

*Receptacle.*—Color: Green Group 143A. Shape: Funnel. Size: Medium (¼" long ×⅜" wide). Surface: Smooth.

*Peduncle.*—Length: Medium (2¾" to +e,fra 3+ee " wide). Surface: Smooth with a few very small green prickles. Color: Medium green. Strength: Stiff, erect.

Bloom:

*Size.*—Large. Average open size is 4 to 4½ inches.

*Borne.*—Several together in rounded clusters of three to five flowers on 8–12"stems.

*Stems.13* Medium, (14–16").

*Form.*—When first open: High centered. Permanence: All petals curl.

*Petalage.*—Number of petals under normal conditions 25–30.

*Color.*—The upper sides of the petals are Red Group 46C. The reverse sides of the petals are Red Group 46C. The reverse sides of the petals are Red Group 46C. The base of each petal has a small (3/16"×3/16"), Yellow Group 6B half-moon. The major color on the upper side is Red Group 46C.

*Variegations.*—There are occasional white streaks on guard petals (inside) and light pink blotches (on outside).

*Discoloraton.*—At the end of the first day: No change. At the end of the third day: No change. Will stay in full color and opening ot completely reflexed by day ten. By day fifteen some discoloration but still turgid.

*Fragrance.*—Slight.

Petals:

*Texture.*—Thick, leathery.

*Shape.*—Round.

*Form.*—Tips slightly recurved.

*Arrangement.*—Imbricated. Petaloids in the center are few.

*Persistence.*—Hang on and dry.

*Lastingness.*—On the plant: Very long (ten days). As a cut flower: Very long (greater than fourteen days).

Reproductive parts:

*Anthers.*—Size: Large. Quantity: Many. Color: Reddish-brown. Arrangement: Regular around styles.

*Filaments.*—Color: Reddish-brown.

*Pollen.*—Color: Gold yellow.

*Styles.*—Color: Reddish.

*Sigmas.*—Color: Greenish-white.

Plant:

*Form.*—Bush.

*Growth.*—Very vigorous; upright; branching; Height in one full season is 4½' tall by 4½' wide.

*Foliage.*—Number of leaflets on normal mid-stem leaves: Seven, occasionally five or nine.

*Size.*—Medium (5"×3½").

*Quantity.*—Abundant.

*Color.*—New foliage: Upper Surface: Greyed-Red 178A; Lower Surface: Greyed Red 178B. Old foliage: Upper Surface: Green Group 139A. Lower Surface: Green Group 139C.

*Shape.*—Broadly oval.

*Texture.*—Upper side: Leathery.

*Edge.*—Serrated.

*Serration.*—Single, small.

*Petiole rachis.*—Color: Green.

*Petiole underside.*—Smooth with occasional prickles.

*Stipules.*—Medium (½" long); serrated, bearded.

*Disease resistance.*—Resistant to mildew and rust under normal growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (¼–⅜"); straight to hooked slightly downward.

*Color when young.*—Red.

Small prickles:

*Quantity.*—On main stalks: None. On laterals: None.

I claim:

1. A new and distinct variety of rose plant of the grandiflora class, substantially as herein shown and described, characterized particulary as to novelty by large flowers presented in open clusters; long vase life; resistance to rust and powdery mildew; vigorous, well branched growth habit; and dark green foliage.

* * * * *

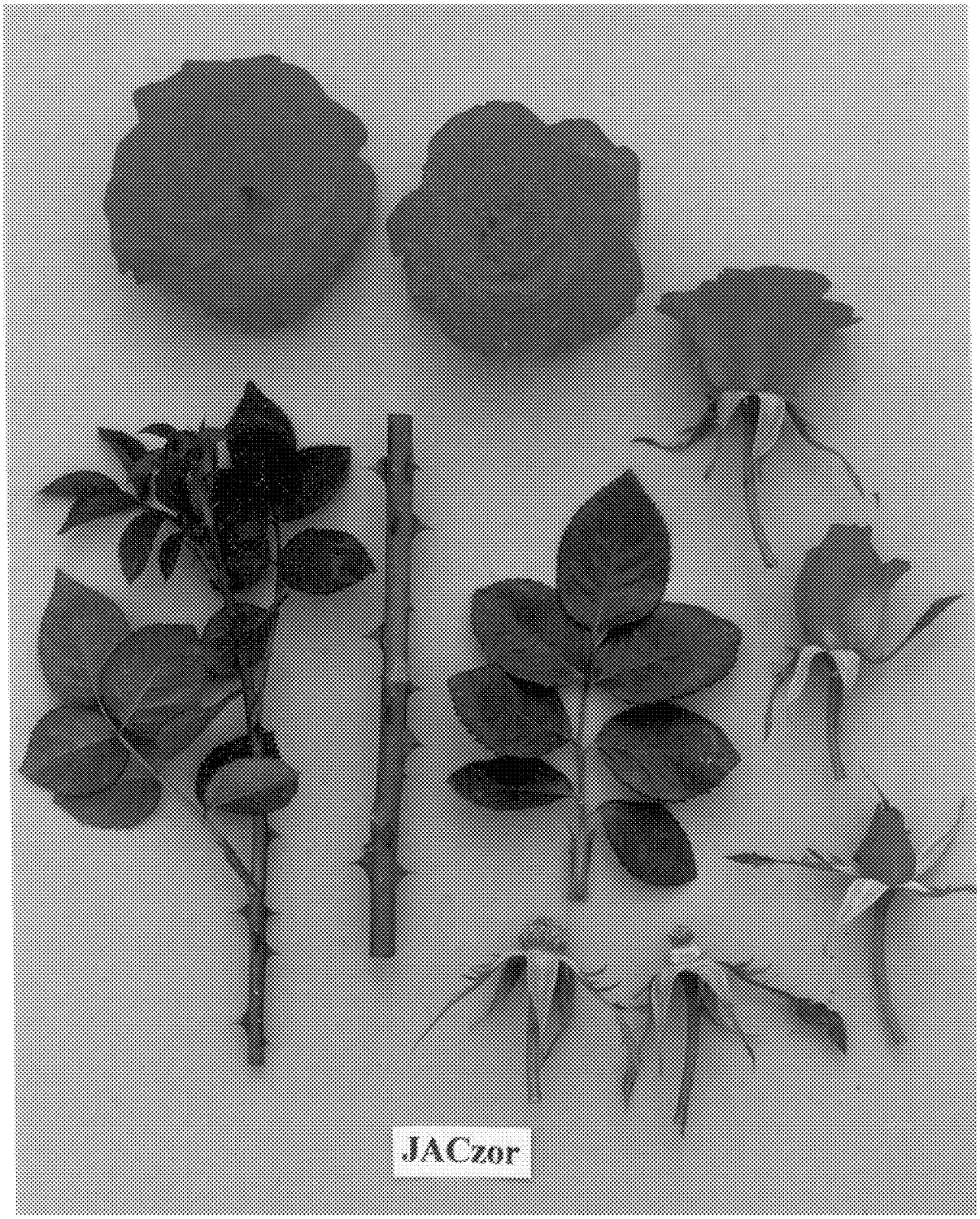
JACzor

UNITED STATES PATENT AND TRADEMARK OFFICE

CERTIFICATE OF CORRECTION

PATENT NO. : PP 11,293
DATED : March 14, 2000
INVENTOR(S) : Keith W. Zary, Ph.D.

It is certified that error appears in the above-identified patent and that said Letters Patent is hereby corrected as shown below:

Column 1:
Lines 8-9, reads "substantiallyachieved". It should read --substantially achieved--.

Column 2:
Line 18, reads "(23/4" to +e.fra 3+ee"wide)". It should read --(2 3/4"to 3")--.
Line 23, reads "4 to 41/2 inches". It should read --4 to 4 1/2 inches--.
Line 25, reads "Stems. 13 Medium. (14-16")". It should read-Stems:-Medium (14-16")--.
Lines 28-29, reads "conditions 25-30". It should read --conditions: 25-30--.
Line 41, reads "ot". It should read --to--.

Column 3:
Line 15, reads "41/2' tall by 41/2' wide". It should read --4 1/2' tall by 4 1/2' wide--.

Signed and Sealed this

Seventeenth Day of July, 2001

Nicholas P. Godici

*Attest:*

*Attesting Officer*

NICHOLAS P. GODICI
*Acting Director of the United States Patent and Trademark Office*